United States Patent [19]
Peck

[11] Patent Number: 5,837,833
[45] Date of Patent: Nov. 17, 1998

[54] MATERIALS AND METHODS FOR DETECTION OF OXALATE

[75] Inventor: Ammon B. Peck, Gainesville, Fla.

[73] Assignee: University of Florida Research Foundation, Inc., Gainesville, Fla.

[21] Appl. No.: 493,197

[22] Filed: Jun. 20, 1995

Related U.S. Application Data

[63] Continuation-in-part of Ser. No. 262,424, Jun. 20, 1994.
[51] Int. Cl.[6] .............................. C12Q 1/68; C12P 19/34; C07H 19/00; C07H 21/04
[52] U.S. Cl. .......................... 536/22.1; 435/6; 435/91.1; 435/91.2; 536/24.3; 536/24.33; 536/237
[58] Field of Search ................................. 536/22.1, 24.3, 536/24.33, 23.7; 435/91.1, 91.2, 6; 935/76, 77, 78

[56] References Cited

U.S. PATENT DOCUMENTS

| | | | |
|---|---|---|---|
| 4,455,371 | 6/1984 | Richardson et al. | 435/25 |
| 4,539,118 | 9/1985 | Crider | 210/683 |
| 5,043,272 | 8/1991 | Hartley | 435/91 |

OTHER PUBLICATIONS

Stratagene Catalog p. 39 (La Jolla, CA, USA) (Stratagene Cloning Systems), 1988.
New England Biolabs Catalog, Beverly, MA, USA, p. 61, 1986.
Lung et al. "Molecular Cloning, DNA Sequence, and Gene Expression of the Oxalyl–Coenzyme A Decarboxylase Gene, oxc, from Bacterium Oxalobacter Formigenes" Journal of Bacteriology vol. 176, No. 8, pp. 2468–2472, 1994.
Lung et al. "Cloning and Expression of the Oxalyl–CoA Decarboxylase Gene From the Bacterium, Oxalobacter Formigenes: Prospects for Gene Therapy to Control Ca–Oxalate Kidney Stone Formation" American Journal of Kidney Diseases, vol. 12, No. 4, pp. 381–385, 1991.
Hodgkinson, A. (1970) "Determination of Oxalic Acid in Biological Material" Clinical Chemistry 16(7):547–557.
Curhan, Gary C. M.D. et al. (1993) "A Prospective Study of Dietary Calcium and Other Nutrients and the Risk of Symptomatic Kidney Stones" N.E.J. Med. 328(12):833–838.
Costello, J. M. Hatch, E. Bourke (1976) "An enzymatic method for the spectrophotometric determination of oxalic acid" J. Lab Clin. Med. 87(5):903–908.
Baetz, A.L., M.J. Allison (1989) "Purification and Characterization of Oxalyl–Coenzyme A Decarboxylase from Oxalobacter formigenes" Journal of Bacteriology 171(5):2605–2608.
Baetz, A.L., M.J. Allison (1990) "Purification and Characterization of Formyl–Coenzyme A Transferase from Oxalobacter formigenes" Journal of Bacteriology 172(7):3537–3540.

(List continued on next page.)

Primary Examiner—Ardin H. Marschel
Assistant Examiner—Jezia Riley
Attorney, Agent, or Firm—Saliwanchik, Lloyd & Saliwanchik

[57] ABSTRACT

The subject invention concerns the novel use of formyl-CoA transferase enzyme together with oxalyl-CoA decarboxylase enzyme for the detection and measurement of oxalate in biological samples. The use of the enzyme system according to the subject invention results in the conversion of oxalate into carbon dioxide and formate. Because the production of formate is directly correlated to the concentration of oxalate present in a sample, the determination of the resulting formate concentration provides an accurate, sensitive and rapid means for detecting even low levels of oxalate. The subject invention further concerns the cloning, sequencing and expression of the genes that encode the formyl-CoA transferase enzyme and the oxalyl-CoA decarboxylase enzyme of *Oxalobacter formigenes*. The subject invention also concerns a method for detecting the presence of *Oxalobacter formigenes* organisms in a sample, and the polynucleotide probes and primers used in the detection method.

8 Claims, 6 Drawing Sheets

OTHER PUBLICATIONS

Yriberri, J., S. Posen (1980) "A Semi–Automatic Enzymic Method for Estimating Urinary Oxalate" Clin. Chem. 26(7):881–884.

Lung, H.Y., A.L. Baetz, A.B. Peck (1994) "Molecular Cloning, DNA Sequence and Gene Expression of the Oxalyl–Coenzyme A Decarboxylase Gene, oxc, from the Bacterium *Oxalobacter formigenes*" Journal of Bacteriology 176(8):2468–2472.

Allen, L.C. et al. (1989) "An Enzymatic Method for Oxalate Automated with the Cobas Fara Centrifugal Analyzer" Clin. Chem. 35(10):2098–2100.

Li, M.G., M.M. Madappally (1989) "Rapid Enzymatic Determination of Urinary Oxalate" Clin. Chem 35(12):2330–2333.

Santamaria, J.R., R. Coll, E. Fuentespina (1993) "Comparative Study of Two Commercial Enzymatic Kits for Determining Oxalate Concentrations in Urine" Clin. Biochem. 26:93–96.

Infantes, J.A. et al. (1991) "Kinetic–enzymatic determination of oxalate in urine by flow injection analysis with double Stopped flow" Analytica Chimica Acta. 242:179–183.

Costello, J.F., Smith, M. (1992) "Determination of Evolved $^{14}CO_2$ in Decarboxylase Reactions with Application to Measurement of [$^{14}$C]Oxalic Acid" Analytical Biochemistry 202:337–339.

Binette, Y., J.–G. Durocher (1985) "Le Dosage des Oxalates Urinaires: Comparaison de Trois Methodes" Ann. Biochem. Clin. Que. 24(3):93–96.

FIG. 3A

```
-180        -172              -139              -124              -100         -81
ATTTGTTTAAATTGACCTGAATCAATATTGCCGGATTGATCTAGGTCAATGATTGATCAAATTGACTTATGTCAATGGTGCCAAATTGACCTAGGTCAACGG
                              -51               -32               -14                        M  S  N  D  D  N  V   20
-80  GATTTTAAAGGGTATGCGGCATACTCGGAATTGACGTTAAACAACCAAAGAAGAAAGGTATTACTCATGAGTAACGACGACAATGT  120
      E  L  T  D  G  F  H  V  L  I  D  A  L  K  M  N  D  I  D  T  M  Y  G  V  V  G  I  P  I  T  N  L  A
 21  AGAGTTGACTGATGGCTTTCATGTTTTGATCGATGCCCTGAAAATGAATGACATCGATACCATGTATGGTGTTGTCGGCATTCCTATCACGAACCTGGCT  220
      R  M  W  Q  D  D  G  Q  R  F  Y  S  F  R  H  E  Q  H  A  G  Y  A  A  S  I  A  G  Y  I  E  G  K  P
121  CGTATGTGGCAAGATGACGGTCAGCGTTTCTACAGCTTCCGTCACGAACAACGCAGGTTATGCAGTTCTATCGCCGGTTACATCGAAGGAAAACCTG  320
      G  V  C  L  T  V  S  A  P  G  F  L  N  G  V  T  S  L  A  H  A  T  T  N  C  F  P  M  I  L  L  S  G  S
221  GCGGTTTGCTTGACCGTTTCCGCCCCCTGGCTTCCCTGAACGGCGTGACTTCCCTGGCTCATGCAACCACCAACTGCTTCCCAATGATCCTGTTGAGCGGTTC  420
      S  E  R  E  I  V  D  L  Q  Q  G  D  Y  E  E  M  D  Q  M  N  V  A  R  P  H  C  K  A  S  F  R  I  N
321  CAGTGAACGTGAAATCGTCGATTTCCAAGACGGCGATTACGAAGAAATGGATCAGATGAATGTTGCACGTCCACACTGCAAAGCTTCTTTCCGTATCAAC  520
      S  I  K  D  I  P  I  G  I  A  R  A  V  R  T  A  V  S  G  R  P  G  G  V  Y  V  D  L  P  A  K  L  F
421  AGCATCAAAGACATTCCAATCGGTATCGCTCGTGCAGTTCGCACCGCTGTATCCGGACGTCCAGGTGGTGTTTACGTTGACTTCCCAGCAAAACTGTTCG  620
      G  Q  T  I  S  V  E  E  A  N  K  L  L  F  K  P  I  D  P  A  P  A  Q  I  P  A  E  D  A  I  A  R  A  A
521  GTCAGACCATTTCTGTAGAAGAAGCTAACAAACTGCTCTTCAAACCAATCGATCCAGCTCCTGCTCAGATTCCTGAAGACGCTATCGCTCGCGCTGC  720
      D  L  I  K  N  A  K  R  P  V  I  M  L  G  K  G  A  A  Y  A  Q  C  D  D  E  I  R  A  L  V  E  E  T
621  TGACCTGATCAAGAACGCCAAACGTCCAGTTATCATGCTTGGTAAAGGCGGTGCAGCTTATGCACAATGCGACGACGAAATCCGGGCACTGGTTGAAGAAACC  820
      G  I  P  F  L  P  M  G  M  A  K  G  L  L  P  D  N  H  P  Q  S  A  A  A  T  R  A  F  A  L  A  Q  C
721  GGCATCCCATTCCTGCCAATGGGTATGGCTAAAGGCCTGCTGCCTGACAACCATCCACAATCCGCTGCTGCAACCCGTGCTTTCGCACTGGCACAGTGT  920
      D  V  C  V  L  I  G  A  R  L  N  W  L  M  Q  H  G  K  G  K  T  W  G  D  E  L  K  K  Y  V  Q  I  D  I
821  ACGTTTGCGTACTGATCGGGCGCTCGTCGTCTGAACTGCTGATGCAGCACGGTAAAGGCAAAACCTGGGGCGACGAACTGAAGAAATACGTTCAGATCGACAT
```

FIG. 3B

```
       Q  A  N  E  M  D  S  N  Q  P  I  A  A  P  V  V  G  D  I  K  S  A  V  S  L  L  R  K  A  L  K  G  A                    1020
 921   CCAGGCTAACGAAATGGACAGCAACAGCCTATCGCTGCACCAGTTGTTGGTGACATCAAGTCCGCCGTTTCCCTGCTCCGCAAAGCACTGAAAGGCGCT
       P  K  A  D  A  E  W  T  G  A  L  K  A  K  V  D  G  N  K  A  K  L  A  G  K  M  T  A  E  T  P  S  G                    1120
1021   CCAAAAGCTGACGCTGAATGGACCGGGGCGCTCTGAAAGCCAAAGTTGACGGCAACAAAGCCAAACTGGCTGCCAAGATGACTGCCGAAACCCCATCCGGAA
       M  M  N  Y  S  N  S  L  G  V  V  R  D  F  M  L  A  N  P  D  I  S  L  V  N  E  G  A  N  A  L  D  N  T                 1220
1121   TGATGAACTACTCCAATTCCCTGGGCGTTGTTCGTGACTTCATGCTGGCAAATCCGGATATTTCCCTGGTTAACGAAGGCGCTAATGCACTCGACAACAC
       R  M  I  V  D  M  L  K  P  R  K  R  L  D  S  G  T  W  G  V  M  G  I  G  M  G  Y  C  V  A  A  A                       1320
1221   TCGTATGATTGTTGACATGCTGAAACCACGCAAACGTCTTGACTCCGGTACCTGGGGTGTTATGGGTATTGGTATGGGTTACTGCGTTGCTGCAGCTGCT
       V  T  G  K  P  V  I  A  V  E  G  D  S  A  F  G  F  S  G  M  E  L  E  T  I  C  R  Y  N  L  P  V  T                    1420
                                                                          [---------TPP Binding Motif----------
1321   GTTACCGGCAAACCGGTTATCGCTGTTGAAGGCGATAGCGCATTCGGTTTCTCCGGTATGGAACTGGAAACTATCTGCCGTTACAACCTGCCAGTTACCG
       V  I  I  M  N  G  G  I  Y  K  G  N  E  A  D  P  Q  P  G  V  I  S  C  T  R  L  T  R  G  R  Y  D  M                    1520
       -----]
1421   GTTATCATCATGAACAATGGTGGTATCTATAAAGGTAACGAAGCAGATCCACAACCAGGCGTTATCTCCTGTACCCGTCTGACCCGTGGTCGTTACGACAT
       M  M  E  A  F  G  G  K  G  Y  V  A  N  T  P  A  E  L  K  A  L  E  E  A  V  A  S  G  K  P  C  L                       1620
1521   GATGATGGAAGCATTTGGCGGTAAAGGTTATGTTGCCAATACTCCAGCAGAACTGAAAGCTCTCGAAGAAGCTGTTGCTTCCGGCAAACCATGCCTG
       I  N  A  M  I  D  P  D  A  G  V  G  S  G  R  I  K  S  L  N  V  V  S  K  V  G  K  K                                    1720
1621   ATCAACGCGATGATCGATCCAGACGCTGGTGTCGAATCTGGCCGTATCAAGAGCCTGAACGTTGTAAGTAAAGTTGGCAAGAAATAATTAGCCCAACTTT
                                                                                                       1705
                                                                                                                              1820
1721   GATGACCGGTTACGACCGGTCACATAAAGTGTTCGAATGCCCTTCAAGTTACTTGAAGGGCATTTTTTTTACCTTGCAGTTTATAAACAGGAAAAATTGT
                                                        1758
                                                                                                                              1908
1821   ATTCAGAGCGGAAAAGCAGATTTAAGCCACGAGAAACATTCTTTTTTATTGAAAATTGCCATAAACACATTTTTAAAGCTGGCTTTTT
```

MATERIALS AND METHODS FOR DETECTION OF OXALATE

CROSS-REFERENCE TO A RELATED APPLICATION

This application is a continuation-in-part of co-pending application Ser. No. 08/262,424, filed Jun. 20, 1994.

This invention was made with government support under National Institutes of Heath Grant No. DK 20586. The government has certain rights in this invention.

BACKGROUND OF THE INVENTION

The present invention relates to novel assay methods for determining the presence or concentration of oxalate in a sample. The present invention further relates to the cloning, sequencing and expression of formyl-CoA transferase, an enzyme used in the novel assay for the detection of oxalate.

Oxalic acid (Oxalate) is a highly toxic natural by-product of catabolism in vertebrate animals and many consumable plants. Unfortunately, a significant portion of humans are unable to properly metabolize oxalate, a condition which may result in the formation of kidney stones in those persons. It is estimated that 70% of all kidney stones are composed of some amount of oxalate. Approximately 12 percent of the U.S. population will suffer from a kidney stone at some time in their lives, and the incidence is rising not only in the United States, but also in Sweden and Japan (Curhan, 1993). Moreover, although a healthy person breaks down or excretes sufficient quantities of oxalate to avoid excessive accumulation of oxalate in the tissues, a number of disease states are known to be associated with malfunctions of oxalate metabolism, including pyridoxine deficiency, renal failure and primary hyperoxaluria, a metabolic genetic disorder that results in the excessive deposition of oxalate in the kidneys.

Persons suffering from and at risk for developing kidney stones, as well as patients with lipid malabsorption problems (e.g. sprue, pancreatic insufficiency, inflammatory intestinal disease, bowel resection, etc.), tend to have elevated levels of urinary oxalate, a fact that has been exploited as a means for identifying individuals at risk. While elevated levels of oxalate may be present in urine, detecting elevated levels of oxalate in serum has not been routine due to the difficulty in detecting the low levels of oxalate present in serum.

Most previous methods for measuring oxalate in a biological sample first require the isolation of the oxalate by precipitation, solvent extraction, or an ion-exchange absorption (Hodgkinson, 1970). Quantitation of the isolated oxalate may be determined by any one of several methods including colorimetry, fluorometry, gas-liquid chromatography or isotope dilution techniques. Because many of the oxalate isolation techniques used in these analytical methods are not quantitative, it is normally necessary to correct for the low recovery of oxalate by adding a $^{14}$C-labeled oxalic acid internal standard, which further complicates the analytical method. All these methods are laborious, and consequently expensive because of the amount of skilled laboratory technician time which must be employed. In addition, isolation of the oxalate may require relatively large sample volumes for starting material.

Recently, several advances in the detection and quantitation of oxalate have been made through the use of (a) oxalate degrading enzymes and (b) high performance liquid chromatography. One commercially-available enzymatic test (Sigma Chemical Company, St. Louis, Mo.) employs oxalate oxidase to oxidize oxalate to carbon dioxide and hydrogen peroxide. The hydrogen peroxide produced can then be measured colorimetrically in a second enzymatic reaction in the presence of peroxidase.

In another enzymatic method for measuring oxalate, oxalate decarboxylase is used to convert oxalate to carbon dioxide and formate. The resultant carbon dioxide can be measured manometrically, by the pH change in a carbon dioxide trapping buffer or by the color change in a pH indicator buffer. Whatever method of carbon dioxide assay is adopted, the time required for diffusion and equilibration of carbon dioxide is much longer than is desirable for a rapid analytical method.

Alternatively, the formate produced by the action of oxalate decarboxylase can be assayed with formate dehydrogenase in an NAD/NADH coupled reaction, as described in Costello, 1976 and Yriberri, 1980. This method is both cumbersome and time-consuming because oxalate decarboxylase and formate dehydrogenase differ in their optimum pH requirements, thus necessitating a pH adjustment during the analysis.

Another commercially available enzymatic test (Boehringer Mannheim) cleaves oxalate to formate and carbon dioxide, then oxidizes the formate to bicarbonate by NAD in the presence of the enzyme formate dehydrogenase. The amount of NADH is determined by means of its absorbance at 334, 340, or 365 nm. Another test ("STONE RISK" by Mission Pharmacal) measures oxalate as a part of a battery of tests for kidney stones.

As illustrated above, the currently existing assays for oxalate suffer from numerous problems, including cost, inaccuracy, reliability, complexity, and lack of sensitivity. Accordingly, it is an object of the subject invention to provide a simple, accurate, and sensitive assay for the detection of low levels of oxalate in a biological sample.

BRIEF SUMMARY OF THE INVENTION

The subject invention concerns the cloning, sequencing, and expression of the formyl-CoA transferase and the oxalyl-CoA decarboxylase genes of *Oxalobacter formigenes*, and the use of the enzymes to detect the presence of oxalate in a sample. The assay of the subject invention provides, for the first time, a rapid, sensitive method to detect even very low concentrations of oxalate in biological samples. Advantageously, the biological samples in which oxalate can be detected include both urine and serum samples. The enzyme system used according to the subject invention converts oxalate to carbon dioxide and formate. In a preferred embodiment of the subject invention, the production of formate is then measured colorimetrically. This assay provides a sensitive, accurate and convenient means for detecting oxalate.

A further aspect of the subject invention is the discovery of the *O. formigenes* genes which encode the formyl-CoA transferase and the oxalyl-CoA decarboxylase enzymes. The discovery of these genes makes it possible to efficiently produce large quantities of pure formyl-CoA transferase and oxalyl-CoA decarboxylase for use in the assay of the subject invention or other appropriate application.

The subject invention also provides a means for detecting the presence of *Oxalobacter formigenes* organisms in a sample. The method of detection provided for herein involves polynucleotide probes which can be used to identify specific Oxalobacter organisms.

The subject invention also concerns the polynucleotide primers and the use thereof for polymerase chain reaction (PCR) amplification of *Oxalobacter formigenes* nucleotide sequences. Amplified Oxalobacter sequences can then be detected using the polynucleotide probes of the subject invention.

BRIEF DESCRIPTION OF THE DRAWINGS

FIG. 3 shows the nucleotide sequence of the oxalyl-CoA decarboxylase gene and flanking regions. The consensus ribosome-binding site lies approximately 10 bases upstream (double-underlined letters) from the putative translation initiation codon (positions 1 to 3). A rho-independent termination sequence lies at positions 1758 to 1790 (double-underlined letters). A putative TPP-binding site appears between positions 1351 and 1437.

BRIEF DESCRIPTION OF THE SEQUENCES

Figure 1A:
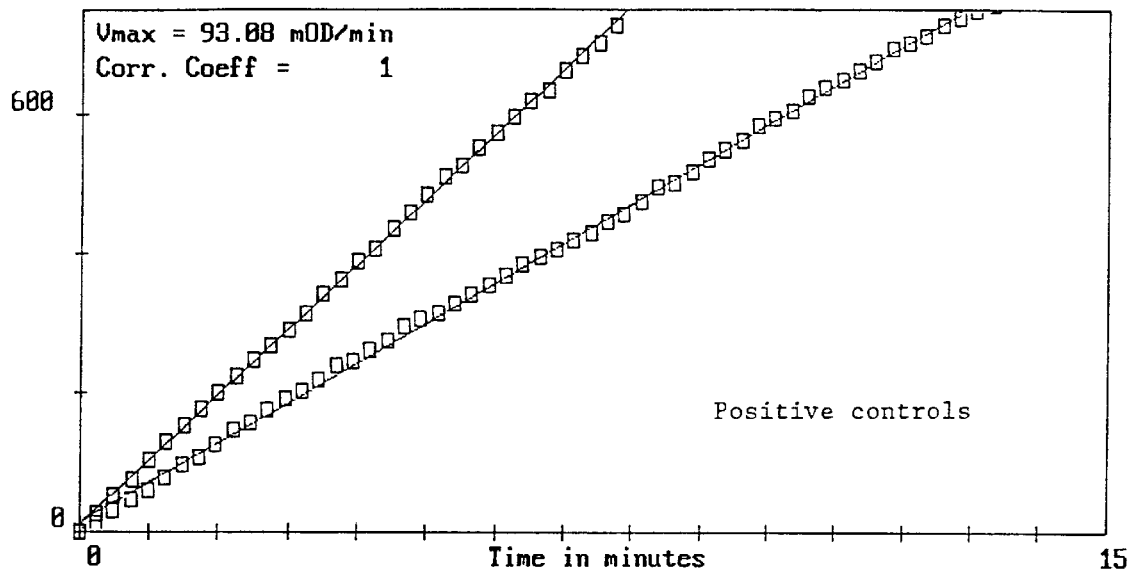
FIG. 1 shows the detection of varying concentrations of oxalate in a sample. Colorimetric absorbance for each sample was plotted over time (minutes). Positive and negative control panels are also shown.
Figure 1B:
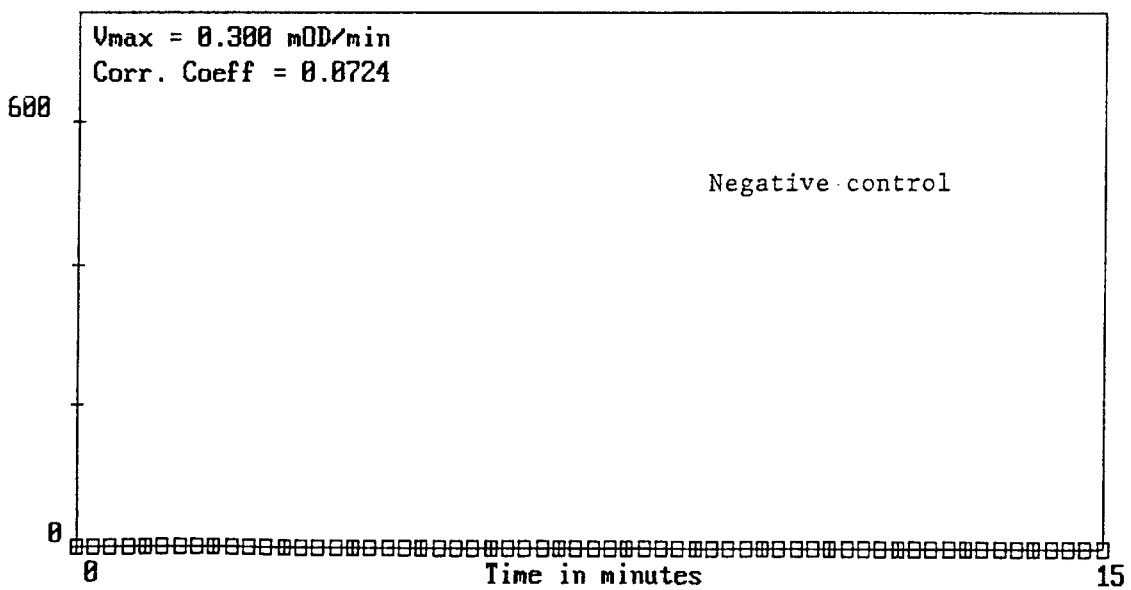
Figure 1C:
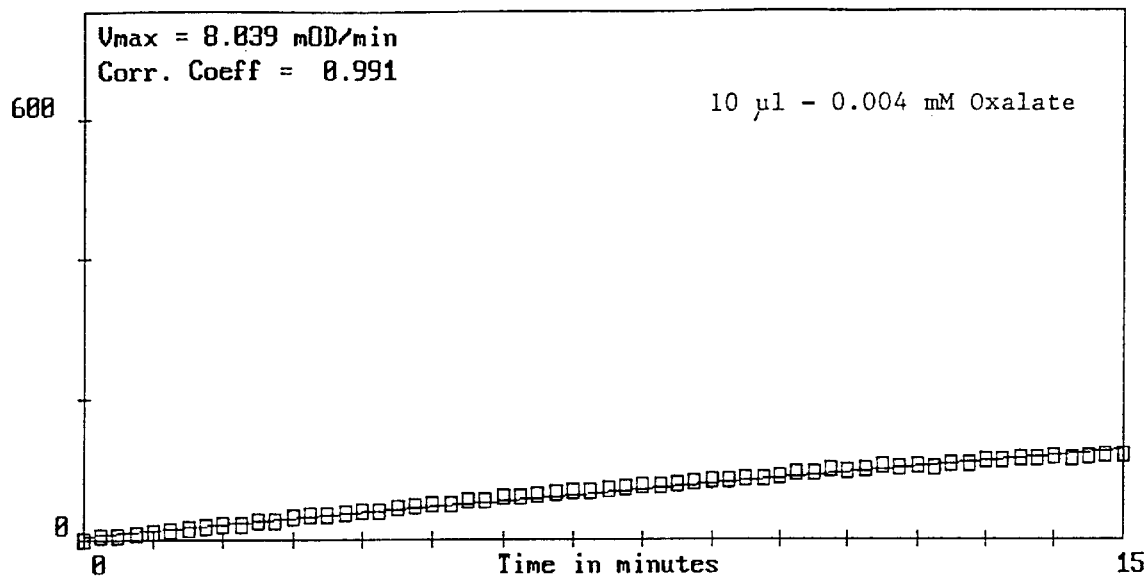
Figure 1D:
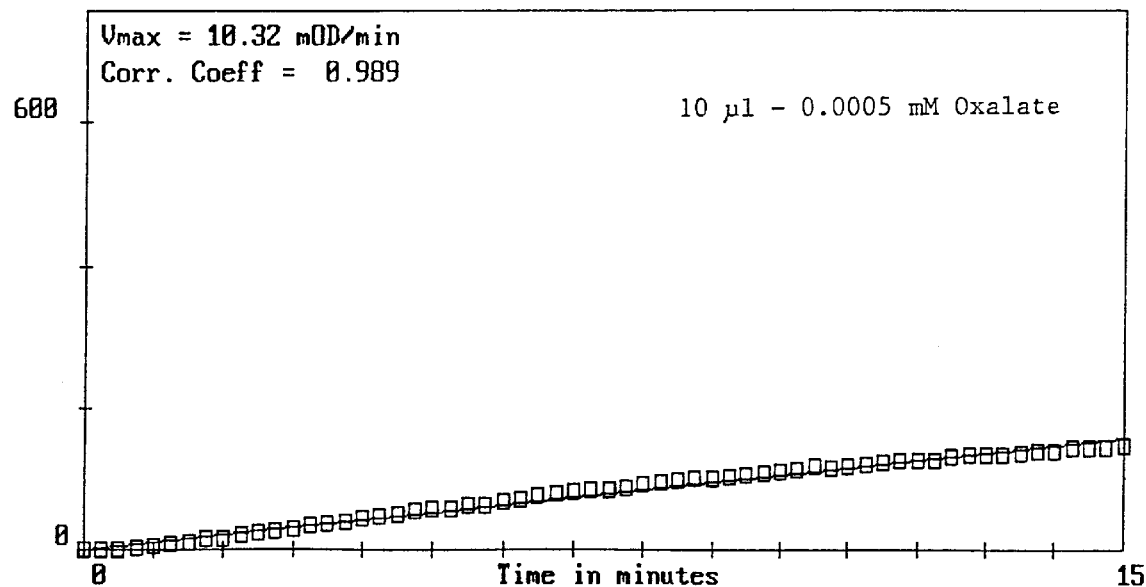
Figure 1E:
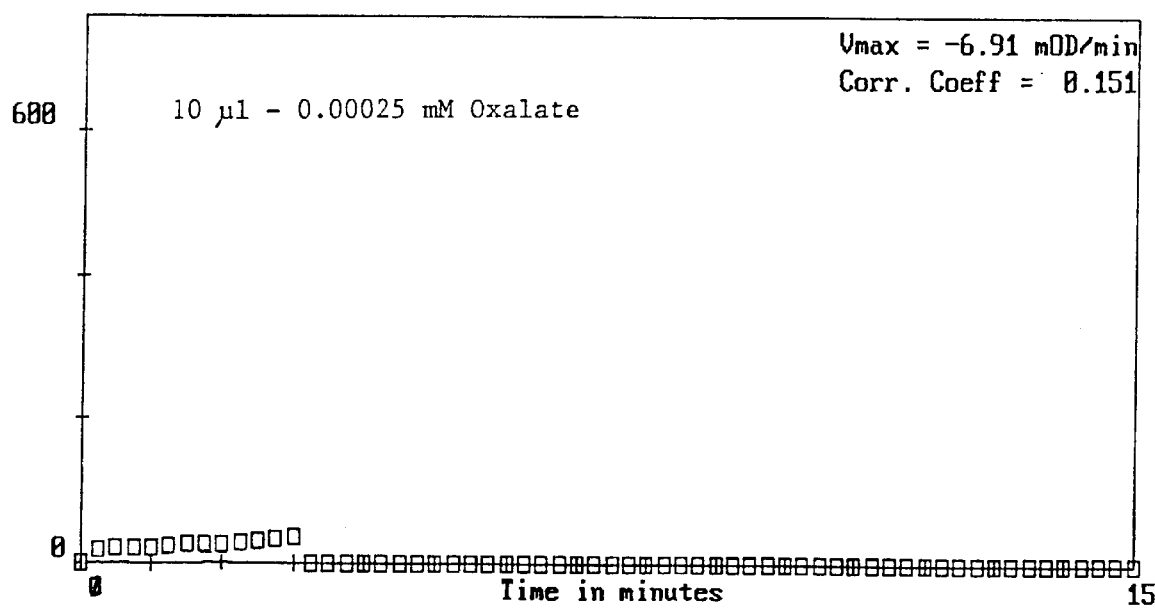
Figure 2:
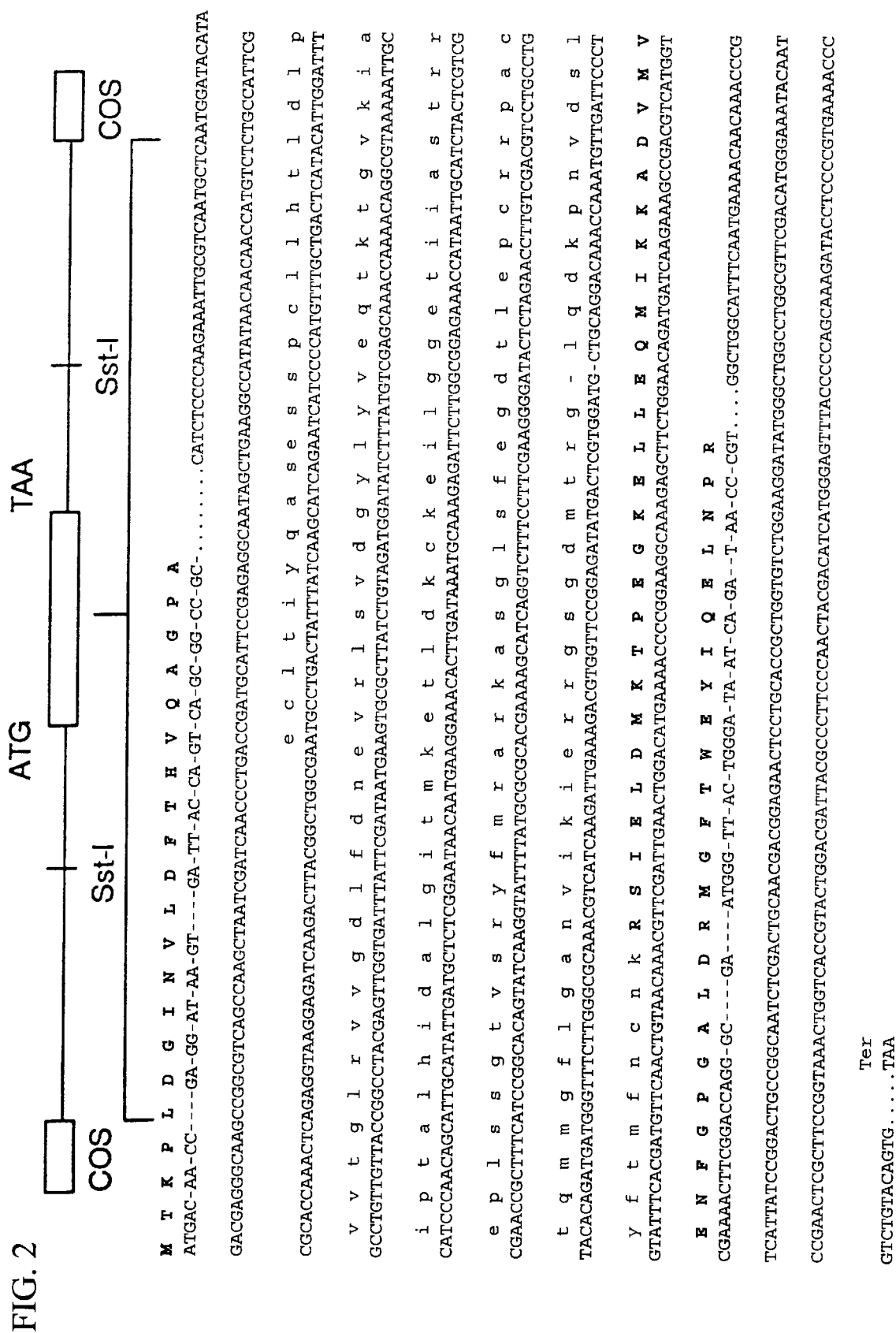
FIG. 2 shows a partial nucleotide sequence of the formyl-CoA transferase gene and a partial amino acid sequence of the formyl-CoA transferase polypeptide. Bolded letters represent amino acid residues determined by N-terminal protein sequencing.

SEQ ID NOS. 1–3 are the known parts of the nucleotide sequence for the formyl-CoA transferase gene (also shown in FIG. 2).

SEQ ID NO. 4 is a polypeptide encoded by SEQ ID NO. 1, which can be used according to the subject invention.

SEQ ID NO. 5 is a polypeptide encoded by SEQ ID NO. 2, which can be used according to the subject invention.

SEQ ID NO. 6 is the nucleotide sequence for the oxalyl-CoA decarboxylase gene (also shown in FIG. 3).

SEQ ID NO. 7 is a polypeptide encoded by SEQ ID NO. 6, which can be used according to the subject invention.

SEQ ID NO. 8 is an oxalyl-CoA decarboxylase probe sequence, which can be used according to the subject invention.

SEQ ID NO. 9 is an oxalyl-CoA decarboxylase probe sequence, which can be used according to the subject invention.

SEQ ID NO. 10 is an oxalyl-CoA decarboxylase 5'-primer, which can be used according to the subject invention.

SEQ ID NO. 11 is an oxalyl-CoA decarboxylase 3'-primer, which can be used according to the subject invention.

DETAILED DESCRIPTION OF THE INVENTION

The subject invention provides an accurate, sensitive assay for oxalate in biological samples such as urine and serum. Elevated levels of oxalate are correlated with urinary tract stone formation, as well as other health problems. Early detection of high levels of oxalate makes it possible to prevent, delay or reduce adverse health consequences through appropriate medication and through modulation of diet.

In the presently described diagnostic system, two enzymes are used to catabolize oxalate to carbon dioxide and formate. Specifically, any oxalate that may be present in a sample being assayed is converted into formate and carbon dioxide ($CO_2$) through the combined action of the enzymes oxalyl-CoA decarboxylase and formyl-CoA transferase. The formate can then be detected using a variety of techniques known in the art. In a preferred embodiment, the production of formate is measured colorimetrically by linking the catabolism of formate with the production of a detectable color change (for example, the formation of a compound that absorbs a particular wavelength of light). The production of formate is directly correlated with the amount of oxalate present in the sample. Therefore, if a known amount of formate is produced using the subject enzyme system, then the amount of oxalate present in the sample can be easily quantitated.

In a preferred embodiment, the enzymes used in the subject invention are expressed by genes from the bacterium *Oxalobacter formigenes*. The genes encoding both oxalyl-CoA decarboxylase (Lung, 1994) and formyl-CoA transferase enzymes have been cloned and expressed, thus providing a readily-available source of reagent material. The subject assay is capable of detecting oxalate levels in a range as low as 0.00025–0.0005 mM (FIG. 1). This level of sensitivity makes the subject assay capable of direct detection of oxalate in serum samples consisting of as little as 10 $\mu$l volume. The described system can be easily automated with standard systems known in the art.

In a preferred embodiment of the subject assay, the enzymatic reaction can be carried out in the wells of flat-bottomed 96-well microtiter plates and read in an automated plate reader. Suitable concentrations of the assay reagents oxalyl-CoA decarboxylase, oxalyl-CoA, $\beta$-NAD, formate dehydrogenase, and the sample to be assayed are added to the microtiter wells. The reaction is then brought to equilibrium (two minute incubation at 37° C. in the plate reader) to permit degradation of any residual formate that may be present in the sample. The formyl-CoA transferase enzyme is then added to the mixture to start the reaction, and the plate is read at 15 second intervals. Formate production is determined by measuring the reduction in NAD in the presence of formate dehydrogenase by detecting changes in absorbance of the sample at 340 nm (Baetz and Allison, 1989). The quantity of oxalate is determined by comparison of the unknown samples with standards having a known amount of oxalate.

Further, the enzymatic reaction of the subject assay will not be initiated until the formyl-CoA transferase, oxalyl-CoA decarboxylase, and oxalyl-CoA are all present within the reaction mixture. Therefore, initiation of the enzymatic reaction can be prevented by withholding one of the above reagents from the reaction mix. Preferably, oxalyl-CoA decarboxylase and oxalyl-CoA are added first, and the reaction is initiated by the addition of formyl-CoA transferase to the mix. However, the order of addition of the three reagents is not material to the function of the assay, so long as one of the reagents is withheld until just prior to the desired initiation point of the assay.

The formyl-CoA transferase and oxalyl-CoA decarboxylase enzyme used in the subject invention can be obtained and purified as a natural product of *Oxalobacter formigenes* (Baetz and Allison, 1989 and 1990). Alternatively, the enzymes can be obtained from host cells expressing the recombinant polynucleotide molecules of the subject invention that encode the enzymes. Other reagents used in the subject assay can be obtained from conventional sources, such as Sigma Chemical Company, St. Louis, Mo. Further, a person of ordinary skill in the art can readily determine the optimal concentrations of the reagents to use in the assay described herein.

A further aspect of the subject invention concerns the cloning, sequencing and expression of the *Oxalobacter*

*formigenes* gene which encodes the formyl-CoA transferase used in the assay that is a subject of the invention. The gene was cloned using degenerate oligonucleotide probes (based on partial amino acid sequencing of tryptic peptides) to screen an Oxalobacter genomic DNA library. The gene encodes a polypeptide having a molecular weight of approximately 40 kD. The subject invention further concerns the cloning, sequencing, and expression of the gene which encodes oxalyl-CoA decarboxylase from *Oxalobacter formigenes*. The nucleotide sequence of the cDNA of formyl-CoA transferase and oxalyl-CoA decarboxylase are shown in FIGS. 2 and 3, respectively (SEQ ID NOS. 1–3 and 6).

Because of the redundancy of the genetic code, a variety of different polynucleotide sequences can encode the formyl-CoA transferase polypeptide disclosed herein. It is well within the skill of a person trained in the art to create alternative polynucleotide sequences encoding the same, or essentially the same, polypeptide of the subject invention. These variant or alternative polynucleotide sequences are within the scope of the subject invention. As used herein, references to "essentially the same" sequence refers to sequences which encode amino acid substitutions, deletions, additions, or insertions which do not materially alter the functional enzymatic activity of the encoded polypeptide. Further, the subject invention contemplates those polynucleotide molecules having sequences which are sufficiently homologous with the DNA sequences shown in FIGS. 2 and 3 (SEQ ID NOS. 1–3 and 6) so as to permit hybridization with those sequences under standard high-stringency conditions. Such hybridization conditions are conventional in the art (see, e.g., Maniatis et al., 1989).

As a person skilled in the art would appreciate, certain amino acid substitutions within the amino acid sequence of the polypeptide can be made without altering the functional activity of the enzyme. For example, amino acids may be placed in the following classes: non-polar, uncharged polar, basic, and acidic. Conservative substitutions, whereby an amino acid of one class is replaced with another amino acid of the same class, fall within the scope of the subject invention so long as the substitution does not materially alter the enzymatic reactivity of the polypeptide. Non-conservative substitutions are also contemplated as long as the substitution does not significantly alter the functional activity of the encoded polypeptide.

The polynucleotides of the subject invention can be used to express the recombinant formyl-CoA transferase enzyme. They can also be used as a probe to detect related enzymes. The polynucleotides can also be used as DNA sizing standards.

The polypeptides encoded by the polynucleotides can be used to raise an immunogenic response to the formyl-CoA transferase enzyme. They can also be used as molecular weight standards, or as inert protein in an assay. The polypeptides can also be used to detect the presence of antibodies immunoreactive with the enzyme.

The polynucleotide sequences of the subject invention may be composed of either RNA or DNA. More preferably, the polynucleotide sequences are composed of DNA.

Another aspect of the subject invention pertains to kits for carrying out the enzyme assay for oxalate. In one embodiment, the kit comprises, in packaged combination and in relative quantities to optimize the sensitivity of the described assay method, (a) the oxalyl-CoA decarboxylase, oxalyl-CoA, β-NAD, and formate dehydrogenase; and (b) formyl-CoA transferase. The kit may optionally include other reagents or solutions, such as buffering and stabilization agents, along with any other reagents that may be required for a particular signal generation system. Other reagents such as positive and negative controls can be included in the kit to provide for convenience and standardization of the assay method.

The subject invention further concerns a method for detecting the presence of *Oxalobacter formigenes* organisms in a sample. Specific polynucleotide probes can be prepared based on the nucleotide sequence of either the oxalyl-CoA decarboxylase or the formyl-CoA transferase gene sequence of *Oxalobacter formigenes*. In a preferred embodiment, the polynucleotide probes are based on the oxalyl-CoA decarboxylase gene sequence.

The polynucleotide probes of the subject invention can be used according to standard procedures and conditions to specifically and selectively detect other polynucleotide sequences that have sufficient homology to hybridize with the probe. In one embodiment of the subject invention, DNA is isolated from bacterial microorganisms in a biological specimen (eg., biopsy, fecal matter, scrapings, etc.) using standard techniques known in the art. The isolated DNA is then screened for hybridization with an Oxalobacter oxalyl-CoA decarboxylase-specific polynucleotide probe. It is not essential to the practice of the subject invention that any particular hybridization technique be employed. For example, various degrees of stringency can be employed during the hybridization, depending on the amount of probe used for hybridization, the level of complementarity (i.e., homology) between the probe and target DNA fragment to be detected. The degree of stringency can be controlled by temperature, ionic strength, pH, and the presence of denaturing agents such as formamide during hybridization and washing. Hybridization methods and conditions are known in the art and are generally described in *Nucleic Acid Hybridization: A Practical Approach* (Hames, B. D., S. J. Higgins, eds.), IRL Press (1985).

The polynucleotide probes of the subject invention include, for example, the oxalyl-CoA decarboxylase probe A (SEQ ID NO. 8) and probe B (SEQ ID NO. 9) specifically exemplified herein. The nucleotide sequences of probe A and probe B are shown below:

Probe A 5'-GAGCGATACCGATTGGA-3'(SEQ ID NO. 8)

Probe B 5'-GCACAATGCGACGACGA-3'(SEQ ID NO. 9)

The polynucleotide probes contemplated in the subject invention also include any polynucleotide molecule comprising a nucleotide sequence capable of specifically hybridizing with the oxalyl-CoA decarboxylase or formyl-CoA transferase genes disclosed herein. As used herein, reference to "substantial homology" or "substantially complementary" refers not only to polynucleotide probes of the subject invention having 100% homology with the nucleotide sequence of the target gene, or fragments thereof, but also to those sequences with sufficient homology to hybridize with the target gene. Preferably, the degree of homology will be 100%; however, the degree of homology required for detectable hybridization will vary in accordance with the level of stringency employed in the hybridization and washes. Thus, probes having less than 100% homology to the oxalyl-CoA decarboxylase or formyl-CoA transferase nucleotide sequences can be used in the subject method under appropriate conditions of stringency. In a preferred embodiment, high stringency conditions are used. In addition, analogs of nucleosides may be substituted for naturally occurring nucleosides within the polynucleotide probes. Such probes having less than 100% homology or containing nucleoside analogs are within the scope of the subject invention. The skilled artisan, having the benefit of the disclosure contained herein, can readily prepare probes encompassed by the subject invention.

In addition, the subject invention also concerns polynucleotide primers that can be used for polymerase chain reaction (PCR) amplification of *Oxalobacter formigenes* nucleotide sequences. PCR amplification methods are well known in the art and are described in U.S. Pat. Nos. 4,683,195; 4,683,202; and 4,800,159. In a preferred embodiment, the polynucleotide primers are based on the oxalyl-CoA decarboxylase gene sequence and can be used to amplify all or portions of the gene. The amplified Oxalobacter sequences can be detected using the probes of the subject invention according to standard procedures known in the art.

The polynucleotide primers of the subject invention include, for example, oxalyl-CoA decarboxylase PCR primer 1 (SEQ ID NO. 10) and PCR primer 2 (SEQ ID NO. 11), specifically exemplified herein. The nucleotide sequences of PCR primers 1 and 2 are shown below:

PCR primer 1 5'-CAGGTTATGCAGCTTCT-3'(SEQ ID NO. 10)

PCR primer 2 5'-GGATGGTTGTCAGGCAG-3'(SEQ ID NO. 11)

The skilled artisan, having the benefit of the disclosure contained herein, can readily prepare other primers of varying nucleotide length and sequence that can be used to amplify the oxalyl-CoA decarboxylase gene.

The polynucleotide probes and primers of the subject invention can be chemically synthesized or prepared through recombinant means using standard methods and equipment. The polynucleotide probes and primers can be in either single- or double-stranded form. If the probe or primer is double-stranded, then single-stranded forms can be prepared from the double-stranded form. The polynucleotide probes and primers may be comprised of natural nucleotide bases or known analogs of the natural nucleotide bases. The probes and primers of the subject invention may also comprise nucleotides that have been modified to bind labeling moieties for detecting the probe or primer or amplified gene fragment.

The polynucleotide molecules of the subject invention can be labeled using methods that are known in the art. The polynucleotides may be radioactively labeled with an isotope such as $^3H$, $^{35}S$, $^{14}C$, or $^{32}P$. The polynucleotides can also be labeled with fluorophores, chemiluminescent compounds, or enzymes. For example, a polynucleotide molecule could be conjugated with fluorescein or rhodamine, or luciferin or luminol. Similarly, the polynucleotide molecule can be conjugated with an enzyme such as horseradish peroxidase or alkaline phosphatase. Polynucleotide molecules can also be detected by indirect means. For example, the polynucleotide may be conjugated with ligands, haptens, or antigenic determinants. The conjugated polynucleotide is then contacted with the ligand receptor, with an anti-ligand molecule that binds to the ligands, or with an antibody that binds to the hapten/antigenic determinant, respectively. The ligand receptor, anti-ligand molecule, or antibody may be directly labeled with a detectable signal system, such as a fluorophore, chemiluminescent molecule, radioisotope, or enzyme. Methods for preparing and detecting labeled moieties are known in the art.

The subject invention also concerns a kit for the detection of *Oxalobacter formigenes* in a sample. A kit contemplated by the subject invention may include in one or more containers: polynucleotide probes, positive and negative control reagents, and reagents for detecting the probes. The kit may also include polynucleotide primers for performing PCR amplification of specific *Oxalobacter formigenes* genes. In a preferred embodiment, the polynucleotide probes and primers are specific for the oxalyl-CoA decarboxylase gene of *O. formigenes*.

Following are examples which illustrate procedures, including the best mode, for practicing the invention. These examples should not be construed as limiting. All percentages are by weight and all solvent mixture proportions are by volume unless otherwise noted.

EXAMPLE 1

Determination of Level of Sensitivity of Enzyme Assay System

Samples containing oxalate at concentrations ranging from 0.004 mM to 0.00025 mM were prepared in 10 µl volumes. The samples were then assayed using the enzyme system of the subject invention in 96-well microtiter plates. Reagents were then added at the following concentrations: $KH_2PO_4$ (pH 6.7), 50 mM; $MgCl_2$, 5 mM; thiamine PPi (TPP), 2 mM; oxalyl-CoA, 0.375 mM; β-NAD, 1.0 mM; formate dehydrogenase, 0.25 IU; and oxalyl-CoA decarboxylase, 0.03 U. The reaction mixture was then incubated at 37° C. for 2 minutes in order to permit the degradation of any residual formate that may be present in the sample mixture. The reaction was then initiated by the addition of formyl-CoA transferase to the sample mixture. Changes in $A_{340}$ were measured every 15 seconds at 37° C. (FIG. 1). Appropriate positive and negative controls were run simultaneously with the assay.

EXAMPLE 2

Detection of *Oxalobacter formigenes* in a Sample

Samples to be tested for the presence of *Oxalobacter formigenes* are obtained from a patient (e.g., biopsy, fecal matter, scrapings), and DNA is isolated from the specimen using standard techniques known in the art. For example, cells can be lysed in an alkali solution, the nucleic acid extracted in phenol:chloroform, and then precipitated with ethanol. The DNA is then fragmented into various sizes using restriction endonuclease enzymes. The DNA fragments are then electrophoretically separated by size on a 0.7–1.0% agarose gel. In an alternative embodiment, the DNA fragments are subjected to PCR prior to gel electrophoresis in order to specifically amplify the oxalyl-CoA decarboxylase gene. Using polynucleotide primers 1 (SEQ ID NO. 10) and 2 (SEQ ID NO. 11) in the PCR method generates a 585 bp amplification product.

After the DNA fragments are separated on the gel, the size-fractionated DNA fragments are transferred to a membrane matrix, such as nitrocellulose, nylon, or polyvinylidene difluoride (PVDF), by Southern blotting. The DNA immobilized on the membrane matrix is single-stranded. Polynucleotide probes of the subject invention are then hybridized with the DNA immobilized on the membrane. In one embodiment, Probe A (SEQ ID NO. 8) or Probe B (SEQ ID NO. 9), labeled with a hapten or antigen such as digoxigenin, is used in the hybridization process. The hybridization can be performed under conditions known in the art. After hybridization of the probe with the DNA fragments on the membrane, the membrane is washed to remove non-hybridized probe. Standard wash conditions are known in the art, and the stringency and number of washes employed may vary.

The membrane is then tested for the presence of hybridized probe. The hybridized probe can be detected using an antibody that binds to the conjugated hapten or antigen on the probe. The antibody can be directly labeled with a detectable fluorophore, chemiluminescent molecule, radioisotope, or enzyme. Alternatively, the antibody can be detected using a secondary reagent that binds to the antibody, such as anti-immunoglobulin, protein A, protein G, etc. The secondary reagent can be labeled with a detectable fluorophore, chemiluminescent molecule, radioisotope, or enzyme. The presence of a detectable hybridization signal indicates the presence of *Oxalobacter formigenes* in a test sample.

It should be understood that the examples and embodiments described herein are for illustrative purposes only and that various modifications or changes in light thereof will be suggested to persons skilled in the art and are to be included within the spirit and purview of this application and the scope of the appended claims.

References

Baetz, A. L., M. J. Allison (1989) "Purification and Characterization of Oxalyl-Coenzyme A Decarboxylase from *Oxalobacter formigenes*," *J. Bacteriol.* 171:2605–2608.

Baetz, A. L., M. J. Allison (1990) "Purification and Characterization of Formyl-Coenzyme A Transferase from *Oxalobacter formigenes*," *J. Bacteriol.* 172:3537–3540.

Curhan, et al. (1993) "A Prospective study of dietary calcium and other nutrients and the risk of symptomatic kidney stones," *N.E.J. Med.* 328:833–838.

Costello, J., M. Hatch, E. Bourke (1976) "An enzymic method for the spectrophotometric determination of oxalic acid," *J. Lab. Clin. Med.* 87(5):903–908.

Hodgkinson, A (1970) "Determination of Oxalic acid in Biological Material," *Clin. Chem.* 16(7):547–557.

Lung, H., A. L. Baetz, A. B. Peck (1994) "Molecular Cloning, DNA Sequence and Gene Expression of the Oxalyl-CoA Decarboxylase Gene, oxc, from the Bacterium *Oxalobacter formigenes*," *J. Bacteriol.* 176(8):2468–2472.

Maniatis, T., E. F. Fritsch, J. Sambrook (1989) *Molecular Cloning: A Laboratory Manual*, 2d Edition, Cold Spring Harbor Laboratory, Cold Spring Harbor, N.Y.

Yriberri, J., L. S. Posten (1980) "A semi-automatic enzymic method for estimating urinary oxalate," *Clin. Chem.* 26(7):881–884.

I claim:

1. A method for detecting *Oxalobacter formigenes* in a sample, comprising the steps of:

(a) amplifying by PCR a DNA fragment of the *Oxalobacter formigenes* genome in said sample using a polynucleotide PCR primer, said PCR primer comprising a nucleotide sequence that is complementary with a polynucleotide sequence of a formyl-CoA transferase gene of *Oxalobacter formigenes,* said formyl-CoA transferase gene comprising a polynucleotide sequence selected from the group consisting of SEQ ID. NO. 1, SEQ ID NO. 2 and SEQ ID NO. 3, wherein said PCR primer is capable of specifically priming PCR amplification of said polynucleotide sequence of said formyl-CoA transferase gene;

(b) contacting said amplified DNA fragment with a polynucleotide probe under conditions sufficient for selective hybridizaiton of said polynucleotide probe with said amplified DNA fragment, wherein said polynucleotide probe comprises a nucleotide sequence that is complementary with a polynucleotide sequence of said amplified DNA fragment, said polynucleotide probe comprising a sufficient number of nucleotides to hybridize under high stringency conditions with said polynucleotide sequence of said amplified DNA fragment; and (c) detecting said polynucleotide probe hybridized to said amplified DNA fragment.

2. The method according to claim 1, wherein said amplified DNA fragment is size-fractionated prior to performing step (b).

3. The method according to claim 1, wherein said amplified DNA fragment is immobilized on a membrane matrix prior to performing step (b).

4. A method for detecting *Oxalobacter formigenes* in a sample, comprising the steps of:

(a) amplifying by PCR a DNA fragment of the *Oxalobacter formigenes* genome in said sample using a polynucleotide PCR primer, said PCR primer comprising a nucleotide sequence that is complementary with a polynucleotide sequence of an oxalyl-CoA decarboxylase gene of *Oxalobacter formigenes*, said oxalyl-CoA decarboxylase gene comprising a polynucleotide sequence of SEQ ID NO. 6, wherein said PCR primer is capable of specifically priming PCR amplification of said polynucleotide sequence of said oxalyl-CoA decarboxylase gene;

(b) contacting said amplified DNA fragment with a polynucleotide probe under conditions sufficient for selective hybridization of said polynucleotide probe with said amplified DNA fragment, wherein said polynucleotide probe comprises a nucleotide sequence that is complementary with a polynucleotide sequence of said amplified DNA fragment, said polynucleotide probe comprising a sufficient number of nucleotides to hybridize under high stringency conditions with said polynucleotide sequence or said amplified DNA fragment; and (c) detecting said polynucleotide probe hybridized to said amplified DNA fragment.

5. The method according to claim 4, wherein said amplified DNA fragment is size-fractionated prior to performing step (b).

6. The method according to claim 4, wherein said amplified DNA fragment is immobilized on a membrane matrix prior to performing step (b).

7. The method according to claim 4, wherein said polynucleotide probe comprises a nucleotide sequence selected from the group consisting of SEQ ID NO. 8, SEQ ID NO. 9, SEQ ID NO. 10, and SEQ ID NO. 11.

8. A polynucleotide PCR primer comprising a nucleotide sequence that is complementary with a polynucleotide sequence of an oxalyl-CoA decarboxylase gene of *Oxalobacter formigenes*, said oxalyl-CoA decarboxylase gene comprising a polynucleotide sequence of SEQ ID NO. 6, wherein said PCR primer is capable of specifically priming PCR amplification of said polynucleotide sequence of said oxalyl-CoA decarboxylase gene and comprises a nucleotide sequence selected from the group consisting of SEQ ID NO.10 and SEQ ID NO. 11.

* * * * *

UNITED STATES PATENT AND TRADEMARK OFFICE
CERTIFICATE OF CORRECTION

PATENT NO. : 5,837,833
DATED : November 17, 1998
INVENTOR(S) : Ammon B. Peck

It is certified that error appears in the above-identified patent and that said Letters Patent is hereby corrected as shown below:

Column 22, line 5: "sequence or said" should read --sequence of said--.

Signed and Sealed this

Sixteenth Day of March, 1999

Attest:

Q. TODD DICKINSON

*Attesting Officer*   *Acting Commissioner of Patents and Trademarks*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
ATGACNAANC  CNNNNGANGG  NATNAANGTN  NNNGANTTNA  CNCANGTNCA  NGCNGGNCCN        60

GCN                                                                          63
```

( 2 ) INFORMATION FOR SEQ ID NO:2:

( i ) SEQUENCE CHARACTERISTICS:
        ( A ) LENGTH: 870 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
CATCTCCCCA  AGAAATTGCG  TCAATGCTCA  ATGGATACAT  AGACGAGGGC  AAGCCGGCGT        60

CAGCCAAGCT  AATCGATCAA  CCCTGACCGA  TGCATTCCGA  GAGGCAATAG  CTGAAGGCCA       120

TATAACAACA  ACCATGTCTC  TGCCATTCGC  GCACCAAACT  CAGAGGTAAG  GAGATCAAGA       180

CTTACGGCTG  GCGAATGCCT  GACTATTTAT  CAAGCATCAG  AATCATCCCC  ATGTTTGCTG       240
```

-continued

| | | | | | |
|---|---|---|---|---|---|
| ACTCATACAT | TGGATTTGCC | TGTTGTTACC | GGCCTACGAG | TTGGTGATTT | ATTCGATAAT | 300
| GAAGTGCGCT | TATCTGTAGA | TGGATATCTT | TATGTCGAGC | AAACCAAAAC | AGGCGTAAAA | 360
| ATTGCCATCC | CAACAGCATT | GCATATTGAT | GCTCTCGGAA | TAACAATGAA | GGAAACACTT | 420
| GATAAATGCA | AAGAGATTCT | TGGCGGAGAA | ACCATAATTG | CATCTACTCG | TCGCGAACCG | 480
| CTTTCATCCG | GCACAGTATC | AAGGTATTTT | ATGCGCGCAC | GAAAAGCATC | AGGTCTTTCC | 540
| TTCGAAGGGG | ATACTCTAGA | ACCTTGTCGA | CGTCCTGCCT | GTACACAGAT | GATGGGTTTC | 600
| TTGGGCGCAA | ACGTCATCAA | GATTGAAAGA | CGTGGTTCCG | GAGATATGAC | TCGTGGATGN | 660
| CTGCAGGACA | AACCAAATGT | TGATTCCCTG | TATTTCACGA | TGTTCAACTG | TAACAAACGT | 720
| TCGATTGAAC | TGGACATGAA | AACCCCGGAA | GGCAAAGAGC | TTCTGGAACA | GATGATCAAG | 780
| AAAGCCGACG | TCATGGTCGA | AAACTTCGGA | CCAGGNGCNN | NNGANNNNAT | GGGNTTNACN | 840
| TGGGANTANA | TNCANGANNT | NAANCCNCGT | | | | 870

( 2 ) INFORMATION FOR SEQ ID NO:3:

( i ) SEQUENCE CHARACTERISTICS:
        ( A ) LENGTH: 259 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

| | | | | | |
|---|---|---|---|---|---|
| GGCTGGCATT | TCAATGAAAA | CAACAAACCC | GTCATTATCC | GGACTGCCGG | CAATCTCGAC | 60
| TGCAACGACG | GAGAACTCCT | GCACCGCTGG | TGTCTGGAAG | GATATGGGCT | GGCCTGGCGT | 120
| TCGACATGGG | AAATACAATC | CGAACTCGCT | TCCGGTAAAC | TGGTCACCGT | ACTGGACGAT | 180
| TACGCCCTTC | CCAACTACGA | CATCATGGGA | GTTTACCCCC | AGCAAAGATA | CCTCCCCGTG | 240
| AAAACCCGTC | TGTACAGTG | | | | | 259

( 2 ) INFORMATION FOR SEQ ID NO:4:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Met Thr Lys Pro Leu Asp Gly Ile Asn Val Leu Asp Phe Thr His Val
1                    5                            10                        15

Gln Ala Gly Pro Ala
                20

( 2 ) INFORMATION FOR SEQ ID NO:5:

( i ) SEQUENCE CHARACTERISTICS:
        ( A ) LENGTH: 226 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

Glu Cys Leu Thr Ile Tyr Gln Ala Ser Glu Ser Ser Pro Cys Leu Leu
1                    5                            10                        15

```
His  Thr  Leu  Asp  Leu  Pro  Val  Val  Thr  Gly  Leu  Arg  Val  Val  Gly  Asp
          20                      25                           30

Leu  Phe  Asp  Asn  Glu  Val  Arg  Leu  Ser  Val  Asp  Gly  Tyr  Leu  Tyr  Val
          35                      40                      45

Glu  Gln  Thr  Lys  Thr  Gly  Val  Lys  Ile  Ala  Ile  Pro  Thr  Ala  Leu  His
     50                      55                      60

Ile  Asp  Ala  Leu  Gly  Ile  Thr  Met  Lys  Glu  Thr  Leu  Asp  Lys  Cys  Lys
65                       70                      75                           80

Glu  Ile  Leu  Gly  Gly  Glu  Thr  Ile  Ile  Ala  Ser  Thr  Arg  Arg  Glu  Pro
                    85                      90                           95

Leu  Ser  Ser  Gly  Thr  Val  Ser  Arg  Tyr  Phe  Met  Arg  Ala  Arg  Lys  Ala
               100                      105                      110

Ser  Gly  Leu  Ser  Phe  Glu  Gly  Asp  Thr  Leu  Glu  Pro  Cys  Arg  Arg  Pro
          115                      120                      125

Ala  Cys  Thr  Gln  Met  Met  Gly  Phe  Leu  Gly  Ala  Asn  Val  Ile  Lys  Ile
     130                      135                      140

Glu  Arg  Arg  Gly  Ser  Gly  Asp  Met  Thr  Arg  Gly  Xaa  Leu  Gln  Asp  Lys
145                      150                      155                      160

Pro  Asn  Val  Asp  Ser  Leu  Tyr  Phe  Thr  Met  Phe  Asn  Cys  Asn  Lys  Arg
                    165                      170                      175

Ser  Ile  Glu  Leu  Asp  Met  Lys  Thr  Pro  Glu  Gly  Lys  Glu  Leu  Leu  Glu
               180                      185                      190

Gln  Met  Ile  Lys  Lys  Ala  Asp  Val  Met  Val  Glu  Asn  Phe  Gly  Pro  Gly
          195                      200                      205

Ala  Leu  Asp  Arg  Met  Gly  Phe  Thr  Trp  Glu  Tyr  Ile  Gln  Glu  Leu  Asn
     210                      215                      220

Pro  Arg
225
```

(2) INFORMATION FOR SEQ ID NO:6:

(i) SEQUENCE CHARACTERISTICS:
        (A) LENGTH: 2088 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
ATTTGTTTAA ATTGACCTGA ATCAATATTG CCGGATTGAT CTAGGTCAAT GAATGCAAAT          60
TGACTTATGT CAATGGTGCC AAATTGACCT AGGTCAACGG GATTTTTAAA GGGTATGCGG         120
CATACTCGGA ATTGACGTTA AACAACGTTT ATCAAACCA  ACCAAGAAA  GGTATTACTC         180
ATGAGTAACG ACGACAATGT AGAGTTGACT GATGGCTTTC ATGTTTTGAT CGATGCCCTG         240
AAAATGAATG ACATCGATAC CATGTATGGT GTTGTCGGCA TTCCTATCAC GAACCTGGCT         300
CGTATGTGGC AAGATGACGG TCAGCGTTTT TACAGCTTCC GTCACGAACA ACACGCAGGT         360
TATGCAGCTT CTATCGCCGG TTACATCGAA GGAAAACCTG GCGTTTGCTT GACCGTTTCC         420
GCCCCTGGCT TCCTGAACGG CGTGACTTCC CTGGCTCATG CAACCACCAA CTGCTTCCCA         480
ATGATCCTGT TGAGCGGTTC CAGTGAACGT GAAATCGTCG ATTTCCAAGA CGGCGATTAC         540
GAAGAAATGG ATCAGATGAA TGTTGCACGT CCACACTGCA AAGCTTCTTT CCGTATCAAC         600
AGCATCAAAG ACATTCCAAT CGGTATCGCT CGTGCAGTTC GCACCGCTGT ATCCGGACGT         660
CCAGGTGGTG TTTACGTTGA CTTCCCAGCA AAACTGTTCG GTCAGACCAT TTCTGTAGAA         720
GAAGCTAACA AACTGCTCTT CAAACCAATC GATCCAGCTC CGGCACAGAT TCTTGCTGAA         780
```

-continued

```
GACGCTATCG CTCGCGCTGC TGACCTGATC AAGAACGCCA AACGTCCAGT TATCATGCTG    840

GGTAAAGGCG CTGCATACGC ACAATGCGAC GACGAAATCC GCGCACTGGT TGAAGAAACC    900

GGCATCCCAT TCCTGCCAAT GGGTATGGCT AAAGGCCTGC TGCCTGACAA CCATCCACAA    960

TCCGCTGCTG CAACCCGTGC TTTCGCACTG GCACAGTGTG ACGTTTGCGT ACTGATCGGC   1020

GCTCGTCTGA ACTGGCTGAT GCAGCACGGT AAAGGCAAAA CCTGGGGCGA CGAACTGAAG   1080

AAATACGTTC AGATCGACAT CCAGGCTAAC GAAATGGACA GCAACCAGCC TATCGCTGCA   1140

CCAGTTGTTG GTGACATCAA GTCCGCCGTT TCCCTGCTCC GCAAAGCACT GAAAGGCGCT   1200

CCAAAAGCTG ACGCTGAATG GACCGGCGCT CTGAAAGCCA AGTTGACGG CAACAAAGCC    1260

AAACTGGCTG GCAAGATGAC TGCCGAAACC CCATCCGGAA TGATGAACTA CTCCAATTCC   1320

CTGGGCGTTG TTCGTGACTT CATGCTGGCA AATCCGGATA TTTCCCTGGT TAACGAAGGC   1380

GCTAATGCAC TCGACAACAC TCGTATGATT GTTGACATGC TGAAACCACG CAAACGTCTT   1440

GACTCCGGTA CCTGGGGTGT TATGGGTATT GGTATGGGCT ACTGCGTTGC TGCAGCTGCT   1500

GTTACCGGCA AACCGGTTAT CGCTGTTGAA GGCGATAGCG CATTCGGTTT CTCCGGTATG   1560

GAACTGGAAA CCATCTGCCG TTACAACCTG CCAGTTACCG TTATCATCAT GAACAATGGT   1620

GGTATCTATA AAGGTAACGA AGCAGATCCA CAACCAGGCG TTATCTCCTG TACCCGTCTG   1680

ACCCGTGGTC GTTACGACAT GATGATGGAA GCATTTGGCG GTAAAGGTTA TGTTGCCAAT   1740

ACTCCAGCAG AACTGAAAGC TGCTCTGGAA GAAGCTGTTG CTTCCGGCAA ACCATGCCTG   1800

ATCAACGCGA TGATCGATCC AGACGCTGGT GTCGAATCTG GCCGTATCAA GAGCCTGAAC   1860

GTTGTAAGTA AAGTTGGCAA GAAATAATTA GCCCAACTTT GATGACCGGT TACGACCGGT   1920

CACATAAAGT GTTCGAATGC CCTTCAAGTT TACTTGAAGG GCATTTTTT ACCTTGCAGT    1980

TTATAAACAG GAAAAATTGT ATTCAGAGCG GAAAAGCAGA TTTAAGCCAC GAGAAACATT   2040

CTTTTTTATT GAAAATTGCC ATAAACACAT TTTTAAAGCT GGCTTTTT                2088
```

(2) INFORMATION FOR SEQ ID NO:7:

(i) SEQUENCE CHARACTERISTICS:
      (A) LENGTH: 568 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:7:

```
Met Ser Asn Asp Asp Asn Val Glu Leu Thr Asp Gly Phe His Val Leu
 1               5                  10                  15

Ile Asp Ala Leu Lys Met Asn Asp Ile Asp Thr Met Tyr Gly Val Val
            20                  25                  30

Gly Ile Pro Ile Thr Asn Leu Ala Arg Met Trp Gln Asp Asp Gly Gln
        35                  40                  45

Arg Phe Tyr Ser Phe Arg His Glu Gln His Ala Gly Tyr Ala Ala Ser
    50                  55                  60

Ile Ala Gly Tyr Ile Glu Gly Lys Pro Gly Val Cys Leu Thr Val Ser
65                  70                  75                  80

Ala Pro Gly Phe Leu Asn Gly Val Thr Ser Leu Ala His Ala Thr Thr
                85                  90                  95

Asn Cys Phe Pro Met Ile Leu Leu Ser Gly Ser Ser Glu Arg Glu Ile
            100                 105                 110

Val Asp Leu Gln Gln Gly Asp Tyr Glu Glu Met Asp Gln Met Asn Val
```

|     |     |     |     | 115 |     |     |     |     | 120 |     |     |     |     | 125 |     |     |     |
| --- | --- | --- | --- | --- | --- | --- | --- | --- | --- | --- | --- | --- | --- | --- | --- | --- | --- |
| Ala | Arg 130 | Pro | His | Cys | Lys | Ala 135 | Ser | Phe | Arg | Ile | Asn 140 | Ser | Ile | Lys | Asp |
| Ile 145 | Pro | Ile | Gly | Ile | Ala 150 | Arg | Ala | Val | Arg | Thr 155 | Ala | Val | Ser | Gly | Arg 160 |
| Pro | Gly | Gly | Val | Tyr 165 | Val | Asp | Leu | Pro | Ala 170 | Lys | Leu | Phe | Gly | Gln 175 | Thr |
| Ile | Ser | Val | Glu 180 | Glu | Ala | Asn | Lys | Leu 185 | Leu | Phe | Lys | Pro | Ile 190 | Asp | Pro |
| Ala | Pro | Ala 195 | Gln | Ile | Pro | Ala | Glu 200 | Asp | Ala | Ile | Ala | Arg 205 | Ala | Ala | Asp |
| Leu | Ile 210 | Lys | Asn | Ala | Lys | Arg 215 | Pro | Val | Ile | Met | Leu 220 | Gly | Lys | Gly | Ala |
| Ala 225 | Tyr | Ala | Gln | Cys | Asp 230 | Asp | Glu | Ile | Arg | Ala 235 | Leu | Val | Glu | Glu | Thr 240 |
| Gly | Ile | Pro | Phe | Leu 245 | Pro | Met | Gly | Met | Ala 250 | Lys | Gly | Leu | Leu | Pro 255 | Asp |
| Asn | His | Pro 260 | Gln | Ser | Ala | Ala | Ala 265 | Thr | Arg | Ala | Phe | Ala 270 | Leu | Ala | Gln |
| Cys | Asp | Val 275 | Cys | Val | Leu | Ile | Gly 280 | Ala | Arg | Leu | Asn | Trp 285 | Leu | Met | Gln |
| His | Gly 290 | Lys | Gly | Lys | Thr | Trp 295 | Gly | Asp | Glu | Leu | Lys 300 | Lys | Tyr | Val | Gln |
| Ile 305 | Asp | Ile | Gln | Ala | Asn 310 | Glu | Met | Asp | Ser | Asn 315 | Gln | Pro | Ile | Ala | Ala 320 |
| Pro | Val | Val | Gly | Asp 325 | Ile | Lys | Ser | Ala | Val 330 | Ser | Leu | Leu | Arg | Lys 335 | Ala |
| Leu | Lys | Gly | Ala 340 | Pro | Lys | Ala | Asp | Ala 345 | Glu | Trp | Thr | Gly | Ala 350 | Leu | Lys |
| Ala | Lys | Val 355 | Asp | Gly | Asn | Lys | Ala 360 | Lys | Leu | Ala | Gly | Lys 365 | Met | Thr | Ala |
| Glu | Thr 370 | Pro | Ser | Gly | Met | Met 375 | Asn | Tyr | Ser | Asn | Ser 380 | Leu | Gly | Val | Val |
| Arg 385 | Asp | Phe | Met | Leu | Ala 390 | Asn | Pro | Asp | Ile | Ser 395 | Leu | Val | Asn | Glu | Gly 400 |
| Ala | Asn | Ala | Leu | Asp 405 | Asn | Thr | Arg | Met | Ile 410 | Val | Asp | Met | Leu | Lys 415 | Pro |
| Arg | Lys | Arg | Leu 420 | Asp | Ser | Gly | Thr | Trp 425 | Gly | Val | Met | Gly | Ile 430 | Gly | Met |
| Gly | Tyr | Cys 435 | Val | Ala | Ala | Ala | Ala 440 | Val | Thr | Gly | Lys | Pro 445 | Val | Ile | Ala |
| Val | Glu 450 | Gly | Asp | Ser | Ala | Phe 455 | Gly | Phe | Ser | Gly | Met 460 | Glu | Leu | Glu | Thr |
| Ile | Cys 465 | Arg | Tyr | Asn | Leu 470 | Pro | Val | Thr | Val | Ile 475 | Ile | Met | Asn | Asn | Gly 480 |
| Gly | Ile | Tyr | Lys | Gly 485 | Asn | Glu | Ala | Asp | Pro 490 | Gln | Pro | Gly | Val | Ile 495 | Ser |
| Cys | Thr | Arg | Leu 500 | Thr | Arg | Gly | Arg | Tyr 505 | Asp | Met | Met | Met | Glu 510 | Ala | Phe |
| Gly | Gly | Lys 515 | Gly | Tyr | Val | Ala | Asn 520 | Thr | Pro | Ala | Glu | Leu 525 | Lys | Ala | Ala |
| Leu | Glu 530 | Glu | Ala | Val | Ala | Ser 535 | Gly | Lys | Pro | Cys | Leu 540 | Ile | Asn | Ala | Met |

```
    Ile  Asp  Pro  Asp  Ala  Gly  Val  Gly  Ser  Gly  Arg  Ile  Lys  Ser  Leu  Asn
    545                      550                      555                      560

Val  Val  Ser  Lys  Val  Gly  Lys  Lys
                        565
```

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GAGCGATACC GATTGGA                                                                      17

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GCACAATGCG ACGACGA                                                                      17

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CAGGTTATGC AGCTTCT                                                                      17

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GGATGGTTGT CAGGCAG                                                                      17